United States Patent
Warnick et al.

(10) Patent No.: US 7,892,239 B2
(45) Date of Patent: Feb. 22, 2011

(54) PIVOTABLE INTERBODY SPACER SYSTEM AND METHOD

(75) Inventors: David R. Warnick, Spanish Fork, UT (US); Thomas M. Sweeney, Sarasota, FL (US); David T. Hawkes, Pleasant Grove, UT (US); Michael D. Ensign, Salt Lake City, UT (US)

(73) Assignee: Beacon Biomedical, LLC, Tequesta, FL (US)

( * ) Notice: Subject to any disclaimer, the term of this patent is extended or adjusted under 35 U.S.C. 154(b) by 132 days.

(21) Appl. No.: 12/051,319

(22) Filed: Mar. 19, 2008

(65) Prior Publication Data

US 2008/0221694 A1 Sep. 11, 2008

Related U.S. Application Data

(63) Continuation-in-part of application No. 11/726,865, filed on Mar. 22, 2007.

(60) Provisional application No. 60/784,546, filed on Mar. 22, 2006, provisional application No. 60/918,789, filed on Mar. 19, 2007.

(51) Int. Cl.
*A61B 17/58* (2006.01)
*A61B 17/60* (2006.01)
*A61F 2/00* (2006.01)

(52) U.S. Cl. .................... 606/99; 606/86 A; 606/279

(58) Field of Classification Search ............. 606/86, 606/99, 60, 86 A, 90, 96, 246, 248, 249, 279; 623/17.11–17.16

See application file for complete search history.

(56) References Cited

U.S. PATENT DOCUMENTS

| 6,599,294 | B2 | 7/2003 | Fuss et al. |
| 6,696,073 | B2 | 2/2004 | Boyce et al. |
| 6,719,794 | B2 | 4/2004 | Gerber et al. |
| 6,942,697 | B2 | 9/2005 | Lange et al. |
| 6,974,480 | B2 | 12/2005 | Messerli et al. |
| 7,018,413 | B2 | 3/2006 | Kruger |
| 7,041,137 | B2 | 5/2006 | Fulton et al. |
| 2003/0139813 | A1 | 7/2003 | Messerli et al. |
| 2004/0097929 | A1* | 5/2004 | Branch et al. ............ 606/61 |
| 2006/0241761 | A1* | 10/2006 | Gately ................ 623/17.11 |
| 2007/0213737 | A1* | 9/2007 | Schermerhorn et al. ....... 606/86 |

\* cited by examiner

*Primary Examiner*—Eduardo C Robert
*Assistant Examiner*—Christina Negrelli
(74) *Attorney, Agent, or Firm*—McHale & Slavin, P.A.

(57) ABSTRACT

A spinal spacer system includes a handle member, an extension member including a first and a second end, wherein the first end of the extension member is coupled to the handle member. Additionally, a coupling device configured to selectively couple a spacer to the second end of the extension member is disposed on the extension member including an angular fixation member configured to fix the spacer in an angular position relative to the handle member. The spinal spacer system also includes an actuator configured to selectively actuate the coupling device and the angular fixation member. The spacer of the present exemplary spinal spacer system includes a proximal end, a distal end, and a rotatably coupleable engagement member disposed on the proximal end of the spacer. According to one exemplary embodiment, the coupling device includes a single protruding member extending from the second end of the extension member.

11 Claims, 14 Drawing Sheets

PIVOTABLE INTERBODY SPACER SYSTEM AND METHOD

RELATED APPLICATIONS

The present application is a Continuation-In-Part application of U.S. patent application Ser. No. 11/726,865, filed Mar. 22, 2007, titled "Pivotable Interbody Spacer," which application claims priority to provisional patent application No. 60/784,546 filed on Mar. 22, 2006 with the same title. Furthermore the present application claims the benefit under 35 U.S.C. §119(e) of U.S. Provisional Patent Application No. 60/918,789 filed Mar. 19, 2007 titled "Pivotable Interbody Spacer System and Method," which applications are incorporated herein by reference in their entireties.

FIELD

The present exemplary system and method relate to bone fixation devices. More particularly, the present system relates to a spinal implant for interbody fusion of the spinal column.

BACKGROUND

The degeneration of the intervertebral disk, in particular, the degeneration of the nucleus pulposus, results in a loss of height in the affected disk space which is associated with a weakening of the annulus fibrosus and of the ligaments. As a consequence the spinal column becomes instable and is more susceptible to horizontal displacement of the vertebral bodies with respect to one another. This horizontal movement of vertebral bodies results in impairments of the nerve roots in this region and/or of the spinal marrow with pain resulting therefrom.

The principle treatment of these symptoms consists of the surgical removal of the nucleus pulposus and the insertion of support bodies in order to restore the normal height of the disk space. While there are a number of traditional systems and methods for inserting support bodies, there are a variety of demands on both the surgeon performing an intervertebral disk procedure and on the spinal spacers themselves.

A Transforaminal Lumbar Interbody Fusion (TLIF) is a surgical procedure that uses a posterior and lateral approach to access the disc space and insert a spacer. To gain access to the disc space, typically a facet joint is removed and access is gained via the nerve foramen. While more technically demanding of the surgeon than other fusion techniques, a TLIF offers a number of clinical advantages.

When compared to a PosteroLateral Fusion (PLF), a TLIF approach leaves much more of the soft tissue intact, which is less traumatic for the patient. Further, a PLF does not provide access to the disc space.

While a PosteroLateral InterBody Fusion (PLIF) provides access to the disc space, a TLIF approach also provides access to the interbody space, but without the need for manipulation of neural elements, reducing the risk of post-operative neural deficit. Additionally, in a TLIF, only a single spacer is placed. More specifically the TLIF spacer is placed in the anterior aspect of the disc space, thus providing space for a substantial fusion mass in the posterior aspect of the disc space where the natural compression occurs.

However, traditional TLIF procedures do suffer from a number of shortcomings. For example, traditional interbody spacers are coupled to an inserter by stationary threads formed in the body of the interbody spacer. Furthermore, in order to place the desired spacer in the anterior aspect of the disc space from an oblique posterior approach, traditional procedures demand that the spacer be released from the inserter and then tamped into place. The two step insertion of this spacer is generally recognized among surgeons as cumbersome and may cause unneeded damage to bone and tissue, thereby increasing patient discomfort and increasing the amount of time sufficient to complete healing.

SUMMARY

According to one exemplary embodiment, a pivotable interbody spacer includes a body defining an inner cavity and a plurality of teeth formed on one end of the spacer. Furthermore, an insertion instrument is associated with the spacer, wherein the insertion instrument includes a retractable latching mechanism and matching interior teeth configured to pivotably mate with the teeth formed on the spacer.

According to another exemplary embodiment, a pivotable interbody spacer system includes an insertion instrument, wherein the insertion instrument includes a retractable latching mechanism and a pivotable tip configured to mate with a spacer Furthermore, according to one exemplary embodiment, a method for pivotably implanting an interbody spacer includes coupling the spacer to a pivoting instrument, inserting the spacer through a nerve foramen, pivoting the spacer to allow further insertion until the spacer is inserted to its final position, and releasing the spacer from the instrument and removing the instrument.

BRIEF DESCRIPTION OF THE DRAWINGS

The accompanying drawings illustrate various exemplary embodiments of the present system and method and are a part of the specification. Together with the following description, the drawings demonstrate and explain the principles of the present system and method. The illustrated embodiments are examples of the present system and method and do not limit the scope thereof.

Figure 1A:
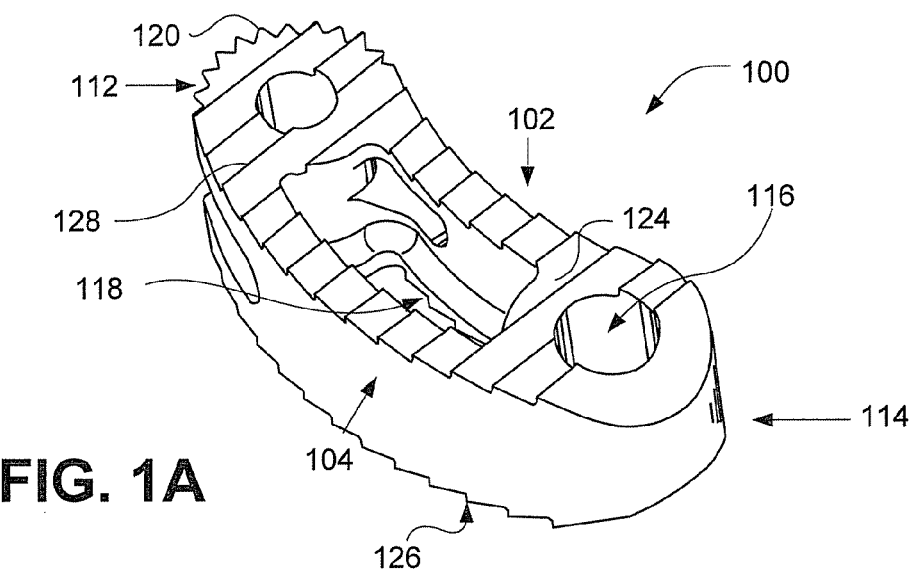
FIGS. 1A, 1B, and 1C are perspective and side views, respectively, of a pivotable interbody spacer, according to exemplary embodiments.

In the drawings, identical reference numbers identify similar elements or features. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Throughout the drawings, identical reference numbers designate similar but not necessarily identical elements.

DETAILED DESCRIPTION

The present specification describes a system and a method for pivotably inserting an interbody spacer, such as during a Transforaminal Lumbar Interbody Fusion (TLIF). According to one exemplary embodiment, a system including a pivotable interbody spacer and insertion instrument configured to pivotably manipulate the interbody spacer are provided herein. According to another exemplary embodiment, a system is provided including an interbody spacer and an insertion instrument with a pivotable element configured to manipulate an interbody spacer. According to yet another exemplary embodiment, a plurality of teeth is formed on at least one end of the spacer and matching teeth are formed on an insertion instrument. An exemplary insertion instrument includes an expandable tip configured to be inserted and mated with a gap within an interbody spacer to aid in selective retention and manipulation of the interbody spacer. In one exemplary embodiment, the insertion instrument includes a male threaded member configured to be mated with a pivotable female threaded cylinder of an interbody spacer. Alternatively, according to yet another exemplary embodiment, the insertion instrument includes a flexible, or pivotable tip, allowing the distal end of the insertion instrument to pivot while coupled to an interbody spacer. Further details of the present exemplary system and method will be provided below, with reference to the figures.

In the following description, certain specific details are set forth in order to provide a thorough understanding of various embodiments of the present system and a method for pivotably inserting an interbody spacer. However, it will be recognized that the present exemplary system and method may be practiced without one or more of these specific details, or with other methods, components, materials, etc. In other instances, well-known structures associated with interbody fusion have not been shown or described in detail to avoid unnecessarily obscuring descriptions of the present exemplary embodiments.

Unless the context requires otherwise, throughout the specification and the appended claims, the word "comprise" and variations thereof, such as, "comprises" and "comprising" are to be construed in an open, inclusive sense, that is as "including, but not limited to."

Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment. Furthermore, the particular features, structures, or characteristics may be combined in any suitable manner in one or more embodiments.

Exemplary Structure

Figure 1B:
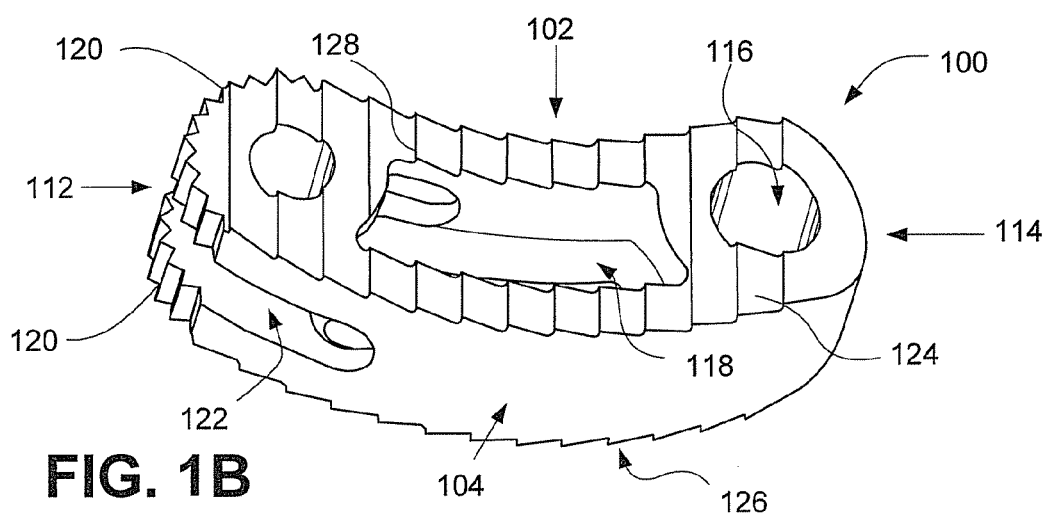
Figure 1C:
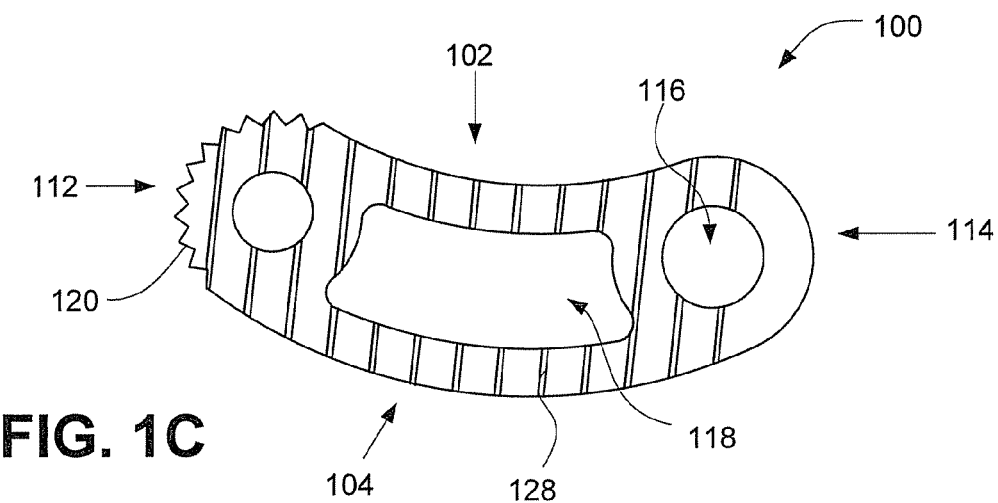

FIGS. 1A, 1B and 1C illustrate an interbody spacer (100), according to one exemplary embodiment. As illustrated in FIGS. 1A, 1B and 1C, the present exemplary interbody spacer (100) is designed for use as an intervertebral spacer in spinal fusion surgery, where portions of an affected disc are removed from between two adjacent vertebrae and replaced with an spacer that provides segmental stability and allows for bone to grow between the two vertebrae to bridge the gap created by disk removal.

As shown, the present exemplary interbody spacer (100) has an arcuate, "rocker-like" shape with concave anterior face (102) and a convex posterior face (104) to facilitate the insertion of the spacer through a narrow approach window into the disk space. As illustrated, the present interbody spacer (100) includes a proximal end (112) that will be closest to a surgeon during use, and a distal end (114) that will likely be the leading edge of insertion during use.

The central portion of the spacer body may have a variety of apertures and bores designed to facilitate and support bone growth. In one exemplary embodiment, the spacer (100) has a substantially hollow center (118). With the advent of bone morphogenic protein (BMP), the spacer is now seen as a potential delivery tool of the BMP. Consequently, many spacers are now hollow. However, the size of the internal cavity of the spacer is limited by the need to limit the size of the spacer and to maximize the surface area of the spacer. Too large of a spacer will not provide space for a fusion mass. Too small of a surface area will lead to subsidence of the spacer into the adjacent vertebral bodies. According to one embodiment, the spacer is hollowed out to increase cavity volume and surface area while minimizing overall size. Consequently, the present exemplary interbody spacer (100) employs geometry that provides for a small spacer with relatively large surface area and internal cavity (118). Other cavities and geometries may be included in the spacer structure, such as cutouts or holes (116).

According to one exemplary embodiment, the interbody spacer (100) has an upper face (124) and an opposing lower face (126). A series of ridges (128) traverse the upper and lower faces (124, 126). The ridges (128) are configured to facilitate the insertion of the interbody spacer (100) by preventing retrograde motion and slippage during the insertion process. After the surgery is complete, the ridges (128) also may provide increase surface area, encourage bone growth, and/or prevent dislocation of the interbody spacer (100).

Additionally, as illustrated in FIGS. 1A and 1B, the present interbody spacer (100) includes frictionally engaging features on at least one end of the spacer (100). According to one exemplary embodiment, any number of protruding features, materials, or rough surface finishes disposed on at least one end of an interbody spacer (100) may be used to pivotably direct an interbody spacer (100) during surgical insertion. Particularly, according to one exemplary embodiment, the interbody spacer (100) has a plurality of teeth (120) disposed about the perimeter of the rounded proximal end (112). The teeth (120) allow for an insertion instrument to firmly grip the interbody spacer (100) and aid in the manipulation of the interbody spacer (100) during insertion. In one exemplary embodiment, the teeth (120), when coupled with an appropriate insertion instrument, may simplify a TLIF procedure by allowing the pivoting and tamping of the interbody spacer (100) without having to release it from the grasp of the insertion instrument.

As shown more particularly in FIG. 1B, the proximal end (112) of the interbody spacer (100) has an access gap (122) that allows access to internal features of the interbody spacer (100). These internal features will be described in detail hereafter; however, the internal features may be formed in any way being configured to allow an insertion tool to secure the interbody spacer. Several internal features configured to allow a pivotable connection between the insertion tool and the interbody spacer are described in detail herein; however, one skilled in the relevant art will recognize that the presently described features or components may be altered to accommodate various insertion tools, allowing the interbody spacer to be secured and pivotably moveable.

In alternative embodiments, the teeth (120) or other frictionally engaging features may be formed inside the access gap (122). For ease of explanation only, the present specification will describe the present system and method in the context of a spacer including external teeth (120) on at least one end thereof. The teeth (120) on the proximal end of the interbody spacer are configured so as to allow an insertion tool to pull the interbody spacer against the insertion tool and lock the angle between the insertion tool and the interbody spacer. In the illustrated embodiment, the distal end (114) of the interbody spacer (100) has a double elliptical leading edge for ease of insertion through the overlying tissues and into the intervertebral space.

Figure 2:
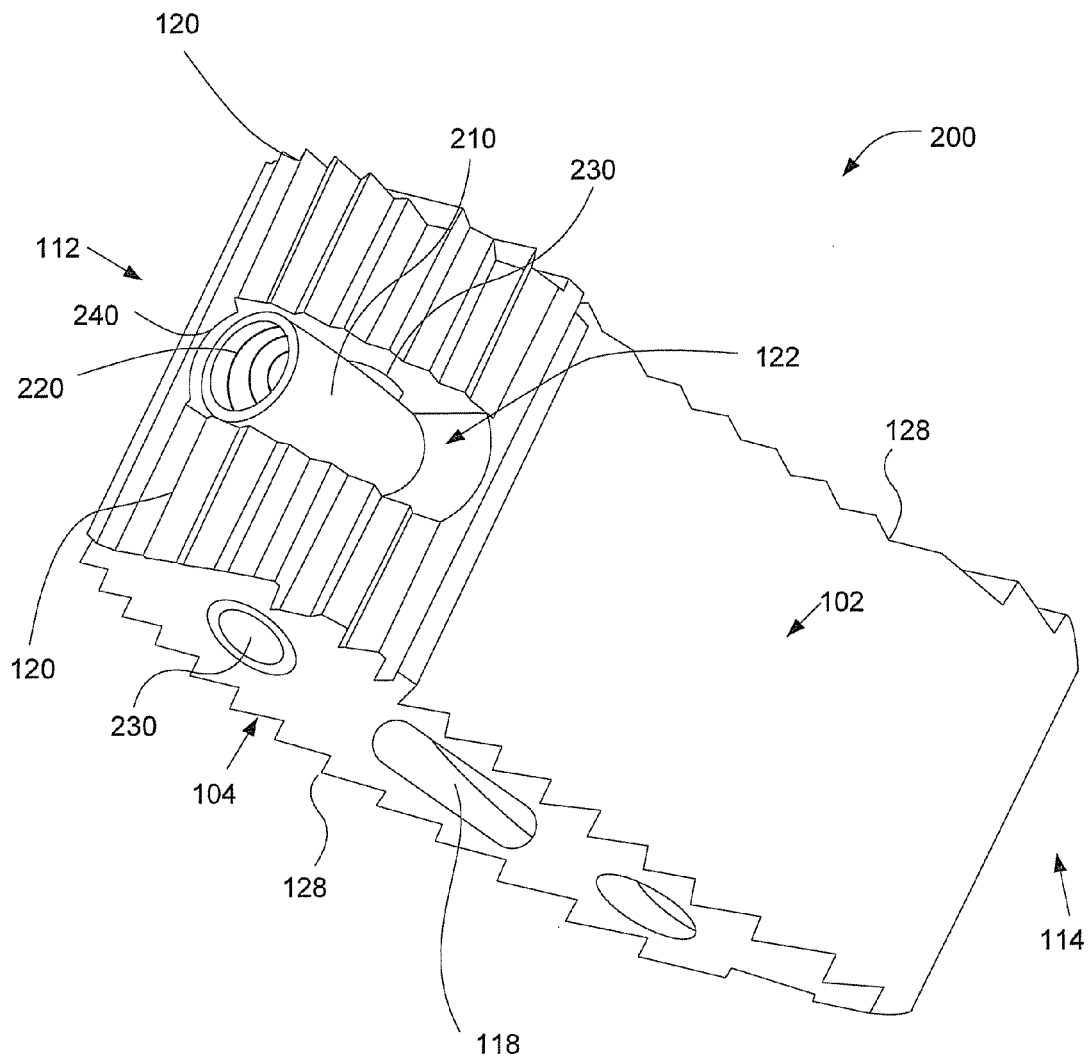
FIG. 2 is a perspective view of a pivotable interbody spacer with a pivotable cylinder configured to receive a male threaded tip, according to one exemplary embodiment.

FIG. 2 illustrates one exemplary embodiment in which the interbody spacer is as previously described with a cylinder (210) within the access gap (122). The cylinder (210) is configured as an engaging feature for the insertion instrument. FIG. 2 shows an interbody spacer with features as illustrated in FIG. 1 and previously described, such as: a plurality of teeth (120) on the proximal end (112), a series of ridges (128) that traverse the upper and lower faces (124, 126), and an internal cavity (118). Alternative embodiments of the exemplary interbody spacer (200) may or may not include these features (112, 116, 120, 128).

As illustrated in FIG. 2, the interbody spacer (200) has an access gap (122) with a cylinder (210) within the gap pivotably attached by a traversing connection, such as the rod (230) illustrated in FIG. 2. The cylinder (210) contains internal threads (220) formed on the inner walls of the cylinder (210) so as to accommodate a connection to a male threaded insertion tool (not shown). Alternatively the cylinder (210) may contain outer threads, allowing it to be connected to an insertion tool with a female threaded tip. The cylinder (210), upon being mated with an insertion tool, may be pivoted about the rod (230) of other connection to the interbody spacer (200), pivoting the cylinder (210) relative to the interbody spacer. The illustrated configuration allows the insertion tool and the interbody spacer to be securely positioned at a relative angle to one another.

As shown in FIG. 2, the access gap (122) is shown with a back wall (240) this may prevent the interbody spacer from reaching some angles relative to the insertion tool, only allowing the angles between the insertion tool and the concave face (102) to be between 0 and 90 degrees. However, in an alternative embodiment the access gap may be contiguous from the concave face (102) to the convex face (104), as best illustrated in FIG. 1B. According to this exemplary embodiment, the no back wall (240) is present to limit the relative angle between the insertion tool and the interbody spacer. While the present exemplary cylinder (210) is described as being coupled to the interbody spacer (200) by a pivoting pin joint, any number of configurations may be used to couple the cylinder to the interbody spacer including, but in no way limited to, a ball and socket joint or any other securing configuration that allows for selective rotational freedom of the spacer with respect to the insertion tool.

Figure 3A:
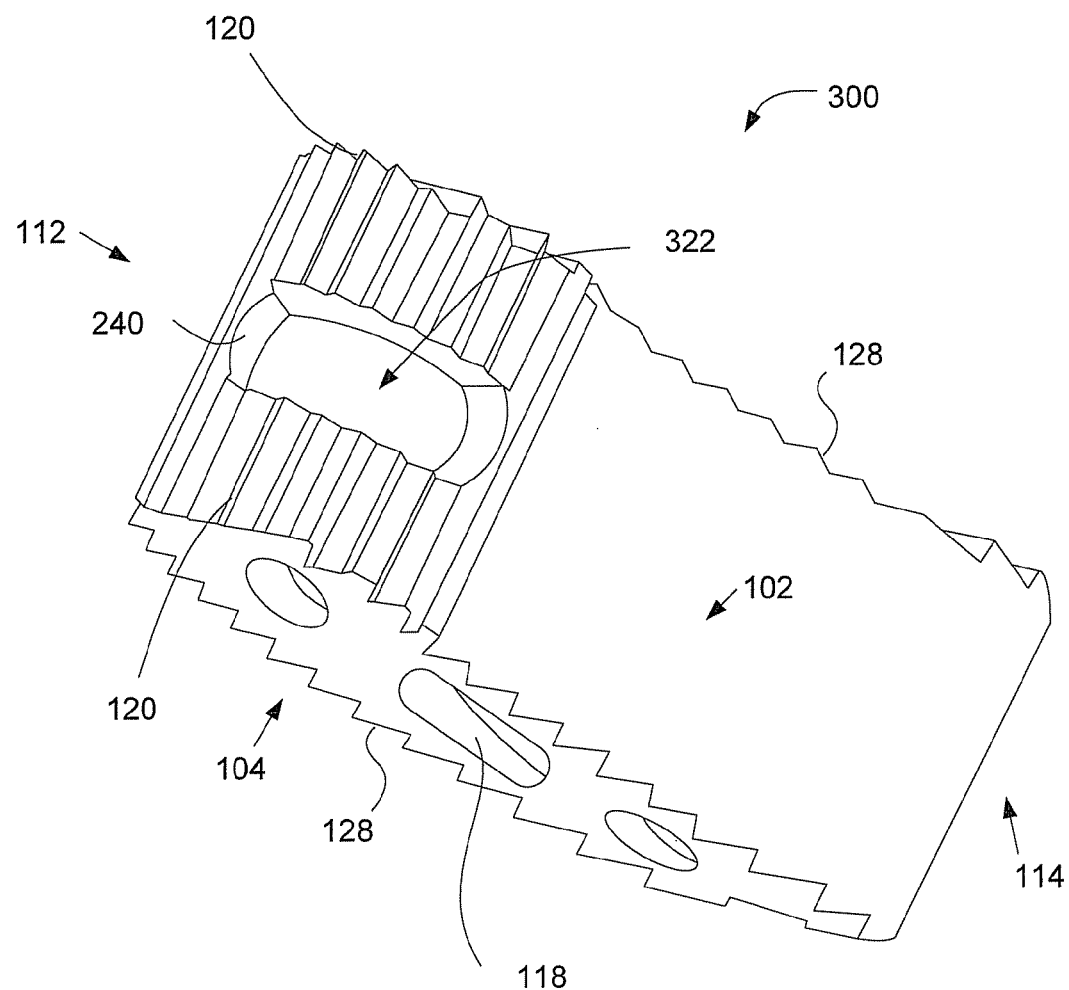
FIGS. 3A and 3B is a perspective view and a cross-sectional view, respectively, of a pivotable interbody spacer with a gap configured to receive an expandable tip, according to one exemplary embodiment

FIG. 3A illustrates an alternative exemplary embodiment of an interbody spacer in which the access gap (122; FIG. 1A) is configured to receive an insertion tool configured with an expandable tip. Particularly, as illustrated in FIG. 3A, the exemplary embodiment includes several of the features as described and illustrated in FIGS. 1A, 1B, and 1C, such as a plurality of teeth (120) on the proximal end (112), a series of ridges (128) that traverse the upper and lower faces (124, 126), and an internal cavity (118). These features may or may not be present on alternative embodiments of an interbody spacer with an access gap (122) configured to receive an insertion tool with an expandable tip. Furthermore, as illustrated in the exemplary embodiment described with reference to FIG. 2, the access gap (322), as shown, does not extend from the concave side (102) of the interbody spacer to the convex side (104). Consequently, a back wall (240) may limit the angle at which the interbody spacer (300) may be held at relative to the insertion tool (not shown). Alternative embodiments configured to receive an insertion tool with an expandable tip may not include a back wall (240) but rather the access gap (322) may be contiguous from the concave side (102) to the convex side (104) as shown in FIG. 1B so as not to limit the angle at which the interbody spacer may be secured.

Figure 3B:
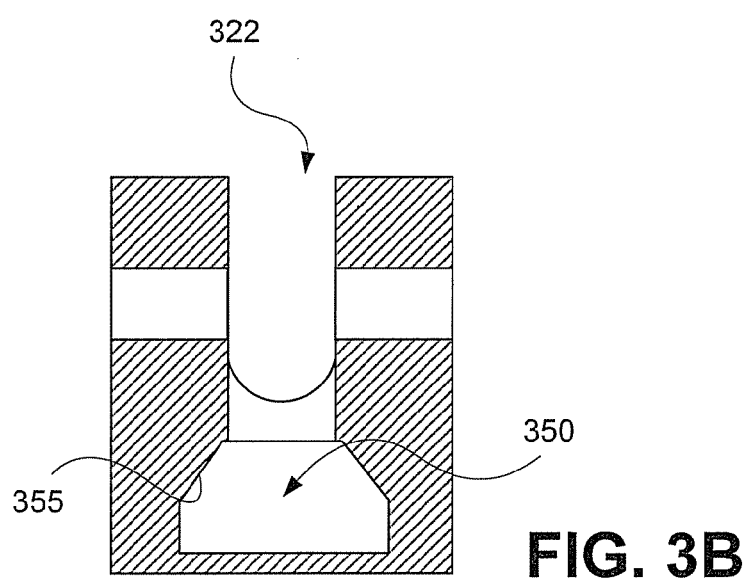

According to the exemplary embodiment illustrated in FIG. 3B, an insertion tool with an expandable tip (not shown) is configured to insert the expandable tip in a contracted state such that the expandable tip will pass through the access gap (322) and into an internal cavity (350). According to one exemplary embodiment, the internal cavity is defined by a plurality of engagement side walls (355) configured to engage an expandable tip in an expanded state, thereby securing the insertion tool within the access gap (322), while allowing some rotational freedom.

Figure 4:
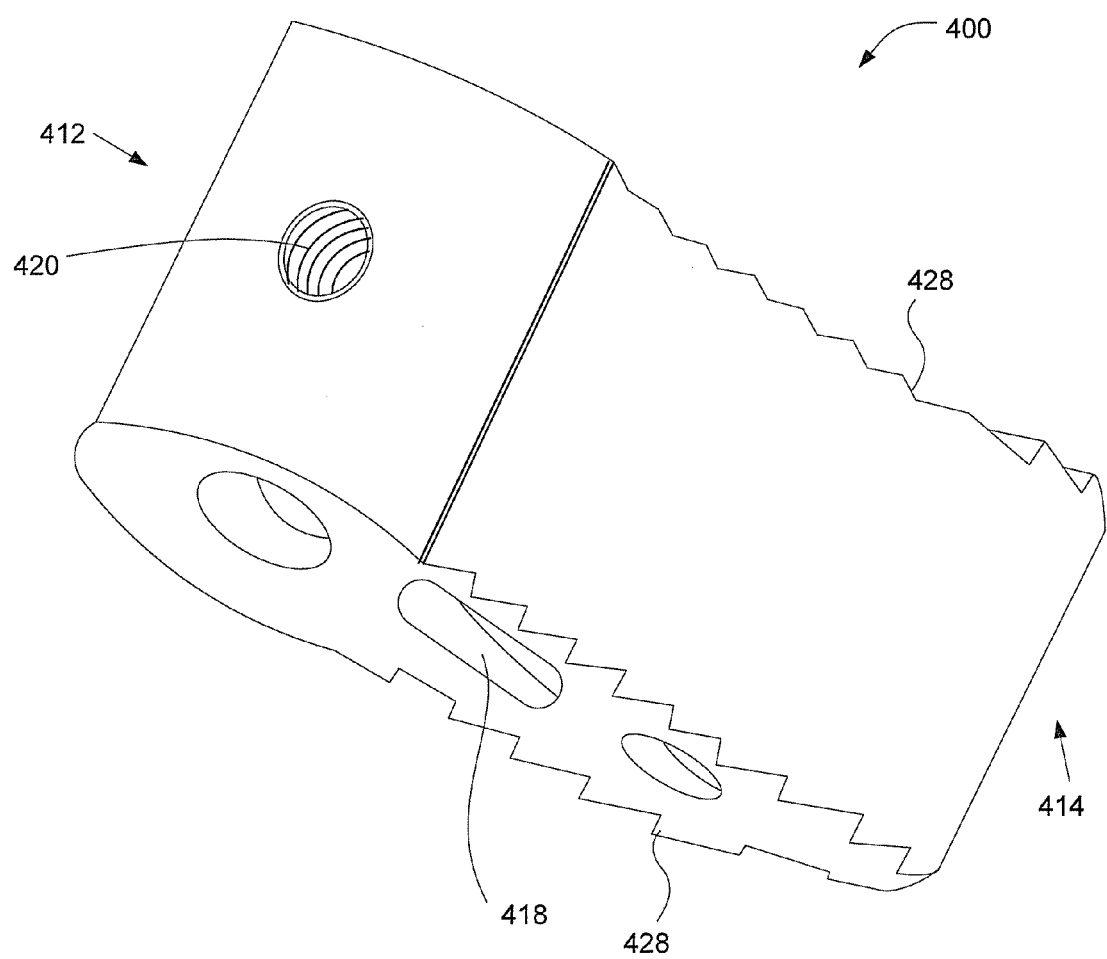
FIG. 4 is a perspective view of an interbody spacer, according to one exemplary embodiment.

FIG. 4 illustrates a traditional interbody spacer (400), for comparison purposes. Particularly, FIG. 4 illustrates a traditional interbody spacer that includes a proximal and a distal end (412, 414). The proximal end commonly includes a stationary, non-rotatable threaded portion configured to receive an insertion tool. In the figure, the threaded portion is drawn as a number of internal threads (420). As shown in FIG. 4, the interbody spacer (400) is drawn to generally represent an interbody spacer commonly used, while also including a number of novel features such as a series of ridges (428) that traverse the upper and lower faces and internal cavities (118), while lacking other novel features disclosed herein such as the teeth (120) illustrated above. The threaded portion (420) configured to be mated with an insertion tool is not pivotable. As FIG. 4 is intended to generally represent traditional interbody spacers many variations of this description of traditional interbody spacers may exist. Relevant to the present exemplary embodiments, it is important to note that the typical interbody spacer has a non-pivoting component configured to be mated with an insertion tool.

Figures 5A, 5B:
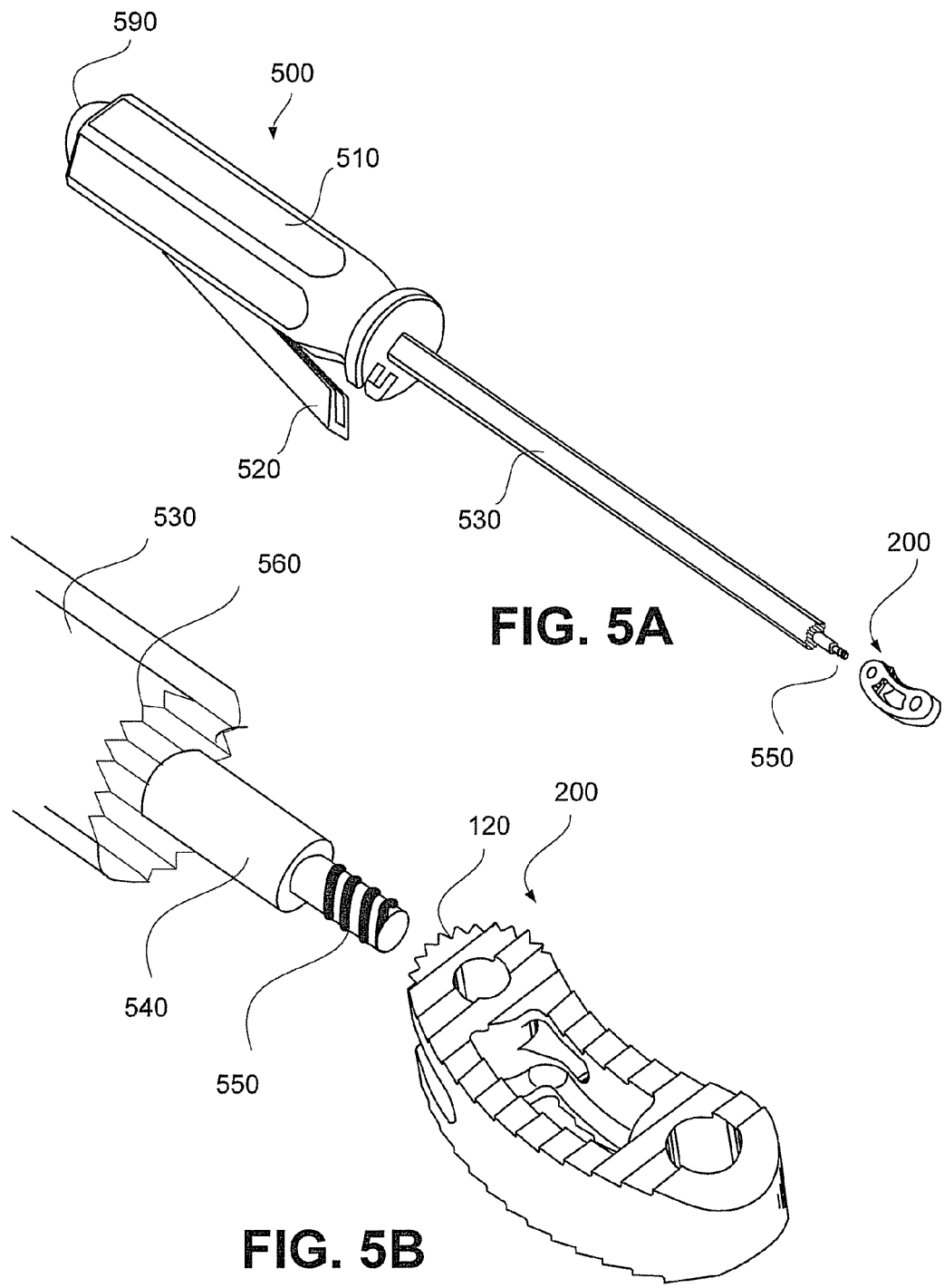
FIGS. 5A and 5B are perspective views of an insertion instrument configured to be threaded onto a pivotable interbody spacer, according to one exemplary embodiment.

FIGS. 5A and 5B illustrate one exemplary embodiment of an insertion instrument (500) that may be used with the pivotable interbody spacer (200) described herein. As illustrated in FIG. 5A, the insertion instrument (500) includes a handle (510) configured to facilitate manual grasping of the insertion instrument (500), a lever (520) pivotably connected to the handle (510), and a shaft (530) extending from one end of the handle (510). At a distal end of the shaft (530) a number of features are disposed which facilitate the securing and subsequent manipulation of the pivotable interbody spacer (500), according to one exemplary embodiment.

As shown in FIG. 5B, the shaft (530) terminates in a number of features configured to facilitate the securing and subsequent manipulation of the interbody spacer (200) including a protruding rod (540) and a male threaded tip (550) and frictional features (560) designed to engage with the frictional features (120) on the interbody spacer (200). In one exemplary embodiment the threaded tip (550) is threaded into the cylinder (210; FIG. 2) of the interbody spacer (200). The threads of the tip are configured so as to be mated with the threads of the cylinder (210; FIG. 2). In an alternative exemplary embodiment the tip of the insertion tool may contain internal female threads and be connected to an interbody spacer with a cylinder containing external male threads. Utilizing an interbody spacer with a pivotable member configured to be connected to the end of the rod (540) in any fashion including, but in no way limited to, protrusions, grooves, snap-together features, or other coupling features are not beyond the scope of the presently disclosed methods.

As shown in FIG. 5B, the insertion tool (500) is threaded onto the interbody spacer to couple the interbody spacer (100) to the insertion tool (200). Additionally, the distal end of the shaft (530) has a concave surface with a plurality of teeth (560) that is configured to receive and engage the plurality of spacer teeth (120) disposed about the perimeter of the convex surface of the proximal end (112) of the interbody spacer (200).

Shown in FIG. 5A is a lever (520) pivotably connected to the handle (510). The lever (520) is mechanically connected through interior mechanisms (not shown) to the protruding rod (540) at the terminal end of the shaft (530). The lever (520) can be moved into two positions that correspond to two different rod positions. A first lever position allows the interbody spacer to pivot relative to the insertion tool. With the lever (520) in the first position the teeth (120) of the interbody spacer are held away from the friction features (560) of the insertion tool, so as to allow the cylinder (210), which is connected to the tip (550), to pivot relative to the interbody spacer.

The lever (520) may also be moved into a second position in which the internal mechanisms (not shown) pull the rod (540) up further within the distal end of the shaft (530) of the insertion tool. As the lever is placed in the second position and the rod is pulled into the shaft, the interbody spacer will be pulled against the shaft of the insertion tool (530). The teeth or frictional members of the interbody spacer (120) will be pulled against the frictional members of the insertion tool (560), thus locking the relative angle of the interbody spacer (200) and the insertion tool (500). The lever (520) may subsequently be placed in the first position again allowing the interbody spacer (200) to pivot once more. As mentioned previously, in contrast to traditional interbody spacers, the present exemplary system and method allow for pivoting of the interbody spacer while maintaining a secure connection between the spacer and the insertion instrument.

Also shown in FIG. 5A is an impaction cap (590) on the end of the handle (510). The impaction cap (590) provides a durable and resilient surface for impacting the insertion instrument (500) to tamp the interbody spacer (200) into position, thereby facilitating insertion and placement.

Figure 6A:
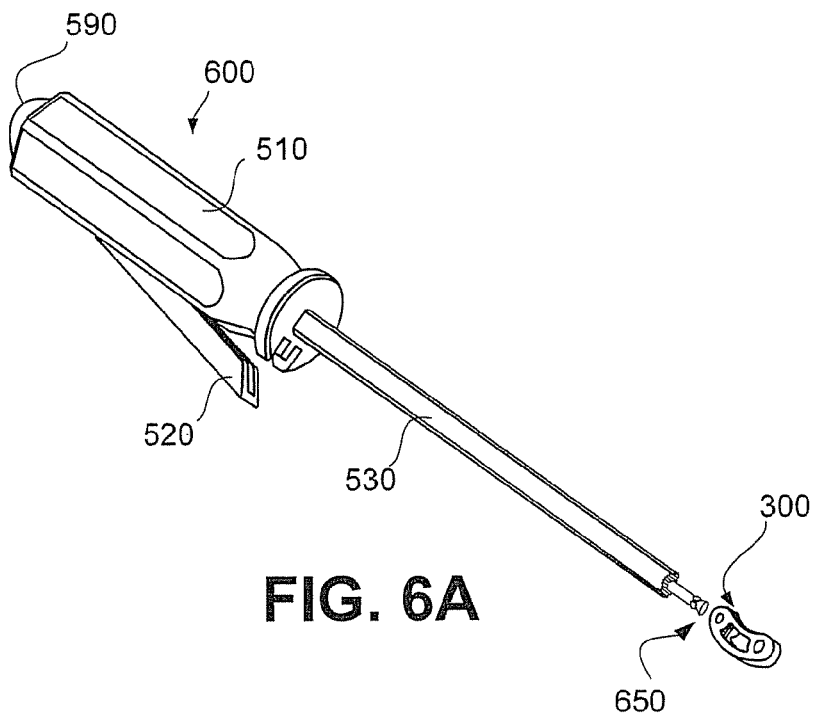
FIGS. 6A through 6C are perspective views and a cross-sectional view, respectively, of an insertion instrument with an expandable tip configured to be inserted into the gap of a pivotable interbody spacer, according to one exemplary embodiment.
Figure 6B:
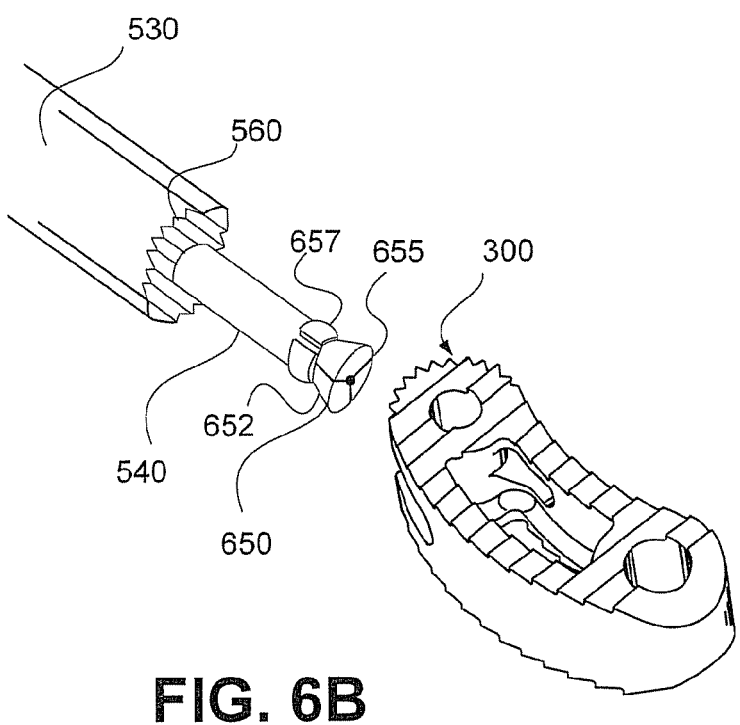
Figure 6C:
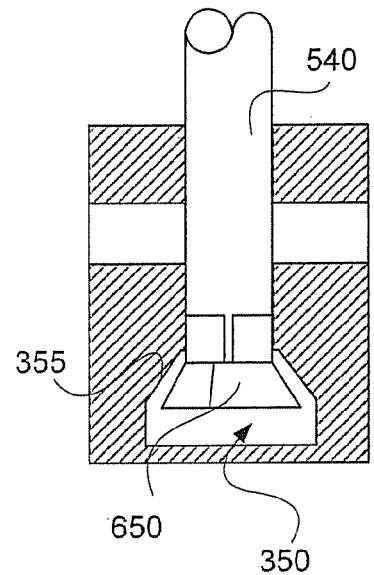

FIGS. 6A through 6C show an exemplary embodiment of an insertion tool that can be used in with a pivotable interbody spacer (300). FIG. 6A shows an insertion tool similar to FIG. 5A, but different in that the distal end terminates in an expandable tip (650) rather than a threaded tip (550). According to one exemplary embodiment, the expandable tip (650) is configured to be mateably connectable to the access gap (322) of the interbody spacer (300).

As shown in FIG. 6B, the shaft (530) terminates in a number of features configured to facilitate the securing and subsequent manipulation of the interbody spacer (200) including a protruding rod (540) and the expandable tip (650) and frictional features (560) designed to engage with the frictional features (120) on the interbody spacer (300). In one exemplary embodiment the expandable tip (650) is put within the access gap (322) in a contracted state. An additional actuator on the insertion tool (not shown) has two positions. A first position in which the expandable tip (650) is contracted and enters the access gap (322), and a second position that causes the tip to expand, securing the expandable tip (650) within the access gap (322).

According to one exemplary embodiment, the expandable tip (650) includes a multi-piece expandable head (655) configured to contract when pulled within the protruding rod (540). According to this exemplary embodiment, when the expandable tip (655) is retracted against the protruding rod (540) and a reinforcement collar (657), tapered outer edges (652) of the expandable tip (650) contact the protruding rod (540) and reinforcement collar (657) causing a contraction of the expandable tip (650). Once the expandable tip (650) is contracted, it will pass through the access gap (322) and into the internal cavity (350) of the interbody spacer (300). Once in the internal cavity (350) of the interbody spacer (300), the expandable tip (650) is allowed to expand and be rotatably secured in the interbody spacer.

Consequently, the interbody spacer (300) is rotatably secured to the insertion tool. In one alternative embodiment the lever (520) on the insertion tool (600) may have three positions: a first position in which the expandable tip (650) is expanded allowing it to enter the access gap (322), a second position in which the expandable tip (650) is expanded rotatably securing the interbody spacer (300) to the insertion tool (600), and a third position in which the rod (540) is pulled into the shaft (530) thereby locking the relative angle between the spacer (300) and the insertion tool (600). In the remaining description the lever (520) has only two positions, requiring an actuator (not shown) that expands and contracts the expandable tip (650).

Additionally, the distal end of the shaft (530) has a concave surface with a plurality of teeth (560) that is configured to receive and engage the plurality of spacer teeth (120) disposed about the perimeter of the convex surface of the proximal end (112) of the interbody spacer (300).

Shown in FIG. 6A is a lever (520) pivotably connected to the handle (510). The lever (520) is mechanically connected through interior mechanisms (not shown) to the protruding rod (540) at the terminal end of the shaft (530). The lever (520) can be moved into two positions that correspond to two different rod positions. A first lever position allows the interbody spacer to pivot relative to the insertion tool. With the lever (520) in the first position the teeth (120) of the interbody spacer are held away from the friction features (560) of the insertion tool, so as to allow the interbody spacer (300) to pivot relative to the insertion tool (600), but remain secured to the insertion tool (600) as the expandable tip (650) remains within the access gap (322) and the internal cavity (350).

The lever (520) may also be moved into a second position in which the internal mechanisms (not shown) pull the rod (540) up further within the distal end of the shaft (530) of the insertion tool. As the lever is placed in the second position and the rod is pulled into the shaft, the interbody spacer will be pulled against the shaft of the insertion tool (530). The teeth or frictional members of the interbody spacer (120) will be pulled against the frictional members of the insertion tool (560), thus locking the relative angle of the interbody spacer (200) and the insertion tool (500). The lever (520) may subsequently be placed in the first position again allowing the interbody spacer (300) to pivot once more.

Also shown in FIG. 6A is an impaction cap (590) on the end of the handle (510). The impaction cap (590) provides a durable and resilient surface for impacting the insertion instrument (600) to tamp the interbody spacer (300) into position.

Figure 7A:
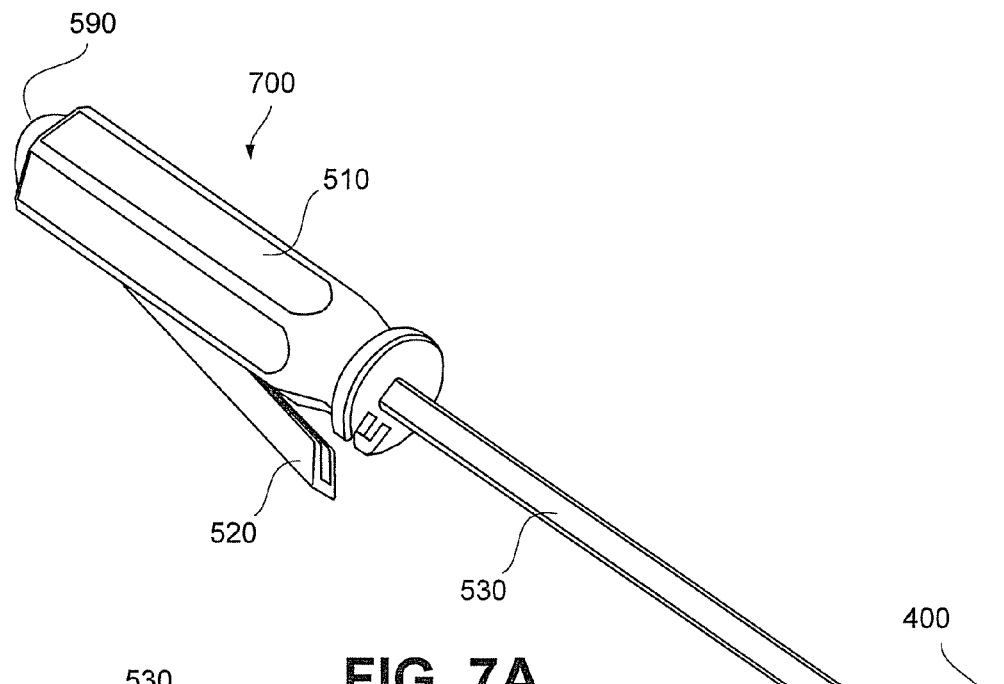
FIGS. 7A and 7B are perspective views of an insertion instrument with a pivotable tip for adapting existing interbody spacers for use as pivotable interbody spacers, according to one exemplary embodiment.
Figure 7B:
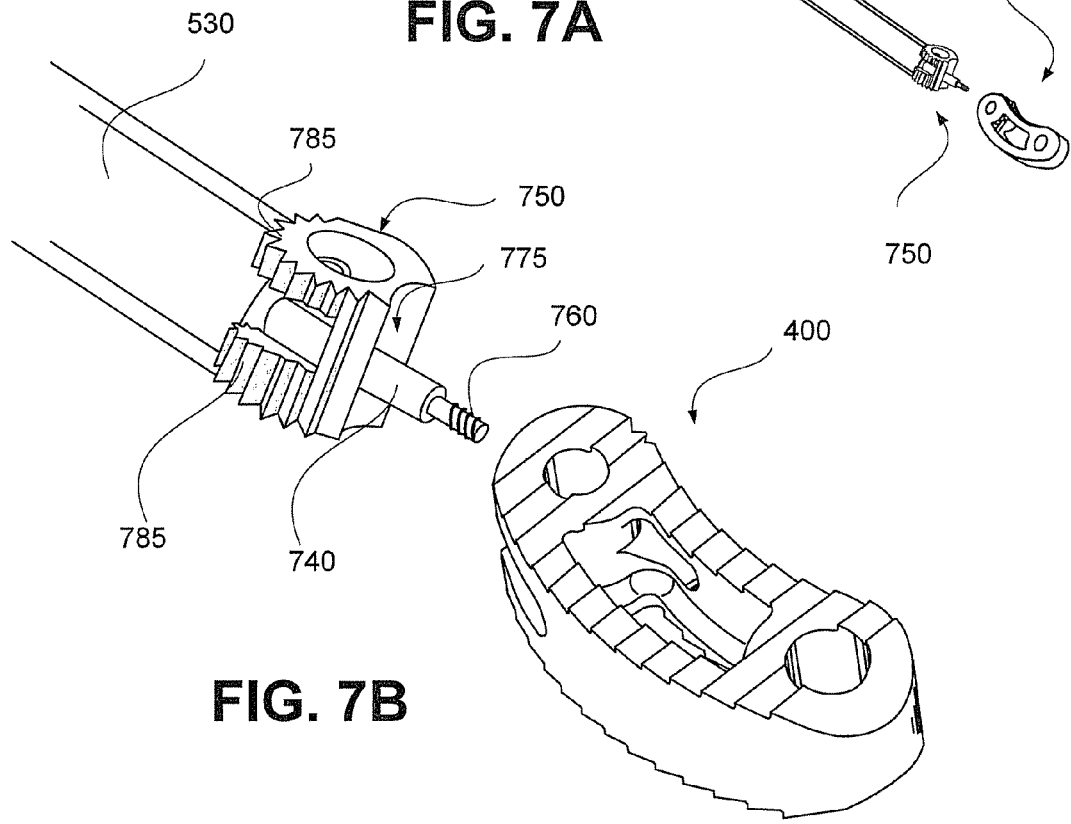

FIGS. 7A and 7B illustrate an alternate exemplary embodiment in which the insertion tool previously described and illustrated in FIGS. 5A, 5B, 6A and 6B is configured so as to allow traditional interbody spacers to be used as pivotable interbody spacers. FIG. 7A shows an insertion tool (700) with an impaction cap (590), a lever (520), a handle (510) and a shaft (530). Each feature described above serve the same functionality as described for the previous insertion tools (500 and 600). Attached to the distal end of the shaft (530) of the exemplary insertion tool (700) is an adapter (750) configured to enable common interbody spacers having non-rotational engagement features to be used as pivotable interbody spacers.

Shown best in FIG. 7B, the exemplary adapter (750) includes a rod (740) passing through the body of the adaptor (750) that protrudes from the shaft (530) of the insertion tool (700). The adapter may be slidably connected to the rod or secured to it. The tip (760) of the rod (740) is configured with threads that connect to a common interbody spacer (400) with stationary mating threads. In the exemplary illustrated example, the interbody spacer (400) is configured to receive a male threaded insertion tool. In the event that an alternate embodiment of a common interbody spacer is used that does not contain a member configured to receive a male threaded insertion tool, the tip of the insertion tool (700) may be modified from a threaded male tip to one that corresponds with the traditional interbody spacer being employed.

FIG. 7B shows the elements of the adapter (750) that allow commonly used interbody spacers (400) to be used as a pivoting interbody spacer. As shown, the adapter is configured with frictional members (785) illustrated as teeth in FIG. 7B. The adapter also has a concave surface (775) on a distal end configured to receive the proximal end (412) of the interbody spacer (400). The rod (740) protruding from the shaft (530) in one exemplary embodiment is flexible, in another embodiment the rod (740) is jointed. Upon attaching the interbody spacer (400) to the tip (760), the adapter (750) may be translated in order to seat the concave portion (775) of the adapter (750) against the proximal end of the interbody spacer (412).

With the lever (520) in the first position the teeth of the adapter (785) are not in contact with the friction features (560) on the distal end of the shaft (530). Consequently, the flexible or jointed rod (740) is free to pivot relative to the shaft (530). Pivoting the rod (740) allows the interbody spacer (400) to be pivoted to an angle relative to the insertion tool (700). By placing the lever (520) in the second position the rod is pulled slightly into the shaft (530), thereby pulling the adapter (750) up against the shaft (530); the frictional features (560) on the shaft engaging the teeth (785) of the adapter, thereby locking the relative angle between the insertion tool (700) and the interbody spacer (400). The lever (520) may subsequently be placed in the first position again releasing the interbody spacer and allowing the angle to be changed, while still securing the interbody spacer to the insertion tool (700).

Figure 8A:
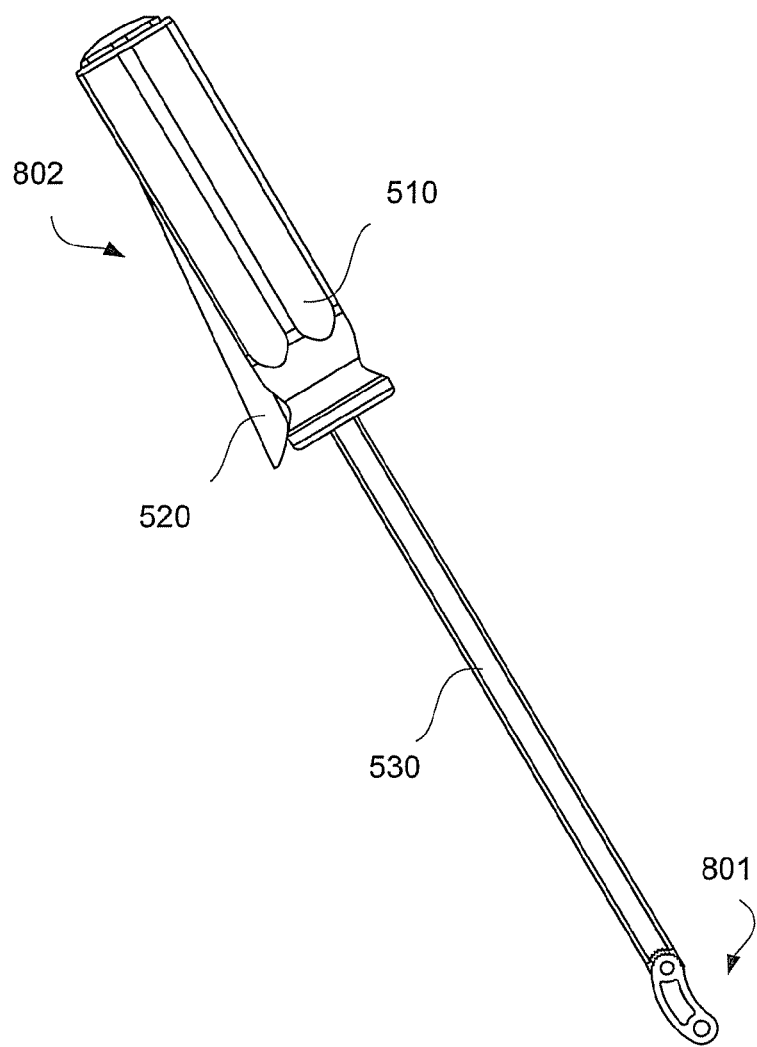
FIGS. 8A and 8B are side views of an insertion instrument rotatably securing a pivotable interbody spacer, according to one exemplary embodiment.
Figure 8B:
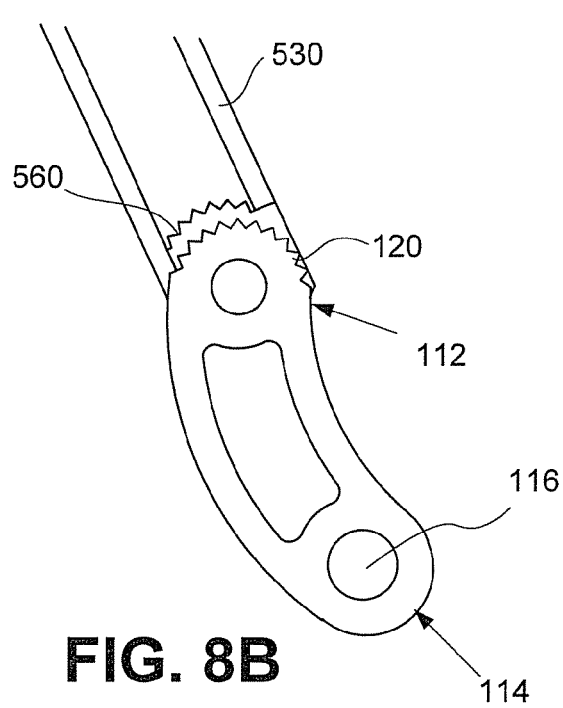

FIGS. 8A and 8B illustrate an exemplary insertion tool (802) with the lever (520) placed in the first position. An interbody spacer (801) is attached to the end of the insertion tool. The insertion tool (802) may represent that of any of the above described insertion tool embodiments as well as alternate embodiments not described in detail. FIGS. 8A and 8B are not intended to show all of the features of the insertion tool or interbody spacers, for example, in the case of the insertion tool of FIGS. 7A and 7B with an adapter (750) some elements are not shown. Rather, the interbody spacer (801) may represent that of any of the above described interbody spacer embodiments as well as alternate embodiments not described in detail. With the interbody spacer (801) attached to the insertion tool (802) and the lever (520) in the first position the interbody spacer is free to pivot relative to the insertion tool as the teeth (120) of the interbody spacer (801) are not engaged with the frictional members (560) of the insertion tool (802). This is best illustrated in FIG. 8B.

Figure 9A:
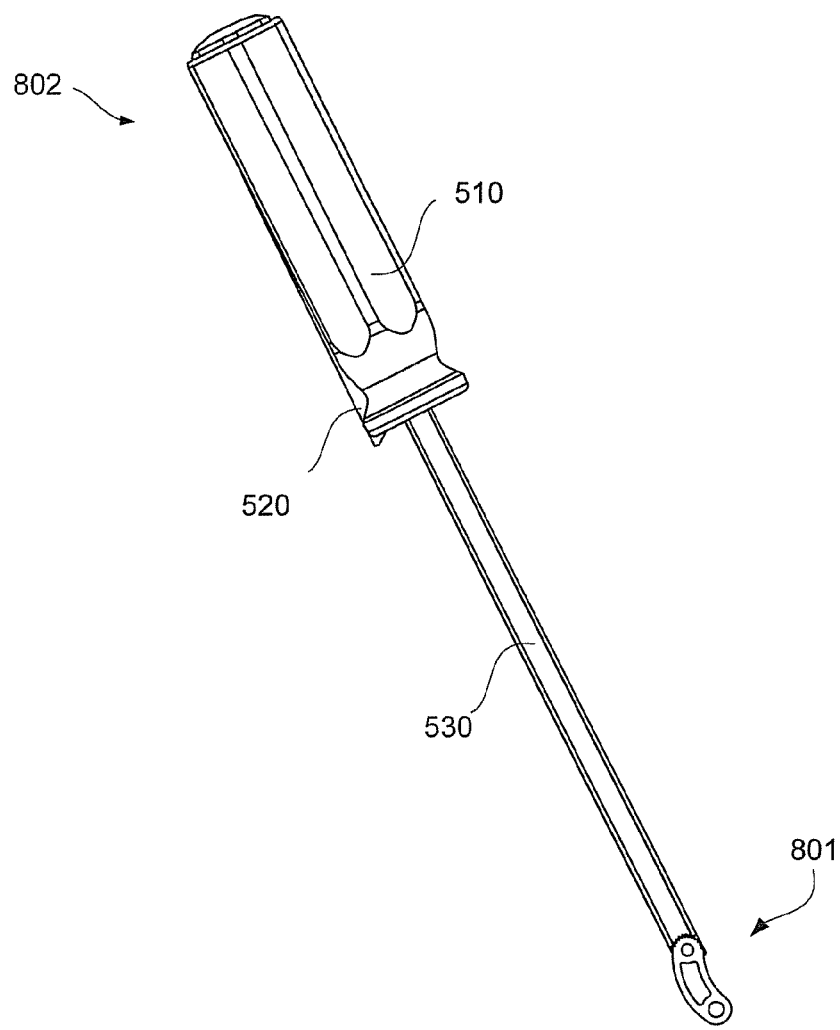
FIGS. 9A and 9B are side views of an insertion instrument fixably securing a pivotable interbody spacer, according to one exemplary embodiment.
Figure 9B:
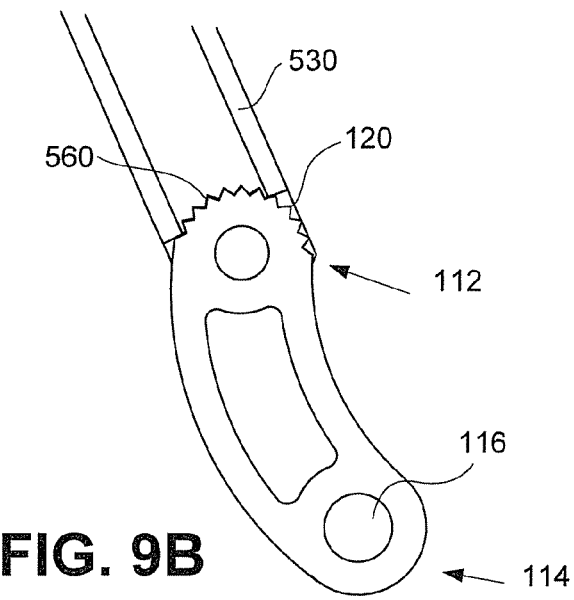

FIGS. 9A and 9B illustrate an insertion tool (802) with the lever (520) placed in the second position. As illustrated in FIGS. 9A and 9B, an interbody spacer (801) is attached to the end of the insertion tool. With the interbody spacer (801) attached to the insertion tool (802) and the lever (520) in the second position the interbody spacer is locked at an angle relative to the insertion tool as the teeth (120) of the interbody spacer (801) are engaged with the frictional members (560) of the insertion tool (802). This is best illustrated in FIG. 9B.

Exemplary Method

Figure 10:
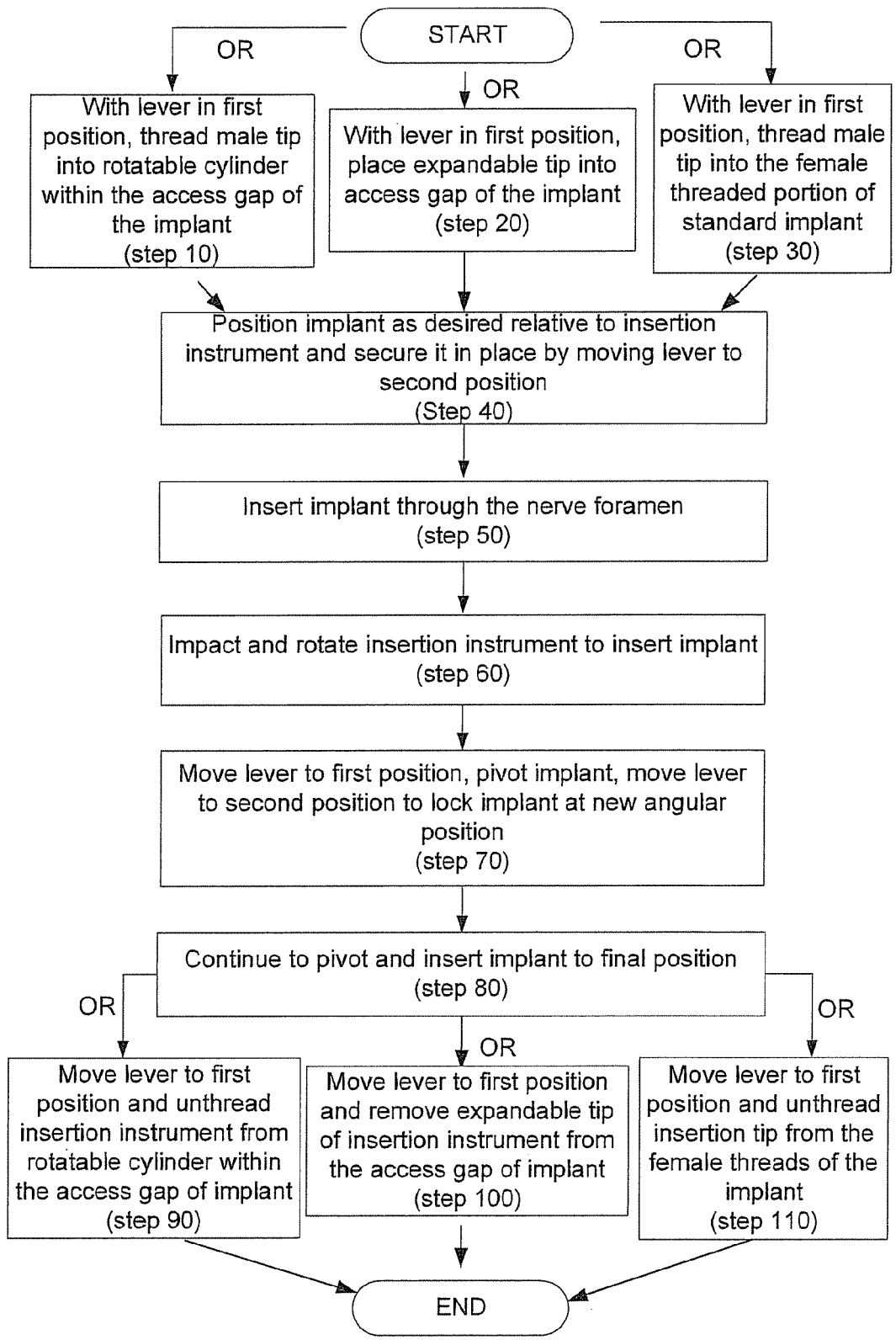
FIG. 10 is a flow chart illustrating a method of pivotably inserting an interbody spacer, according to one exemplary embodiment.
Figure 11:
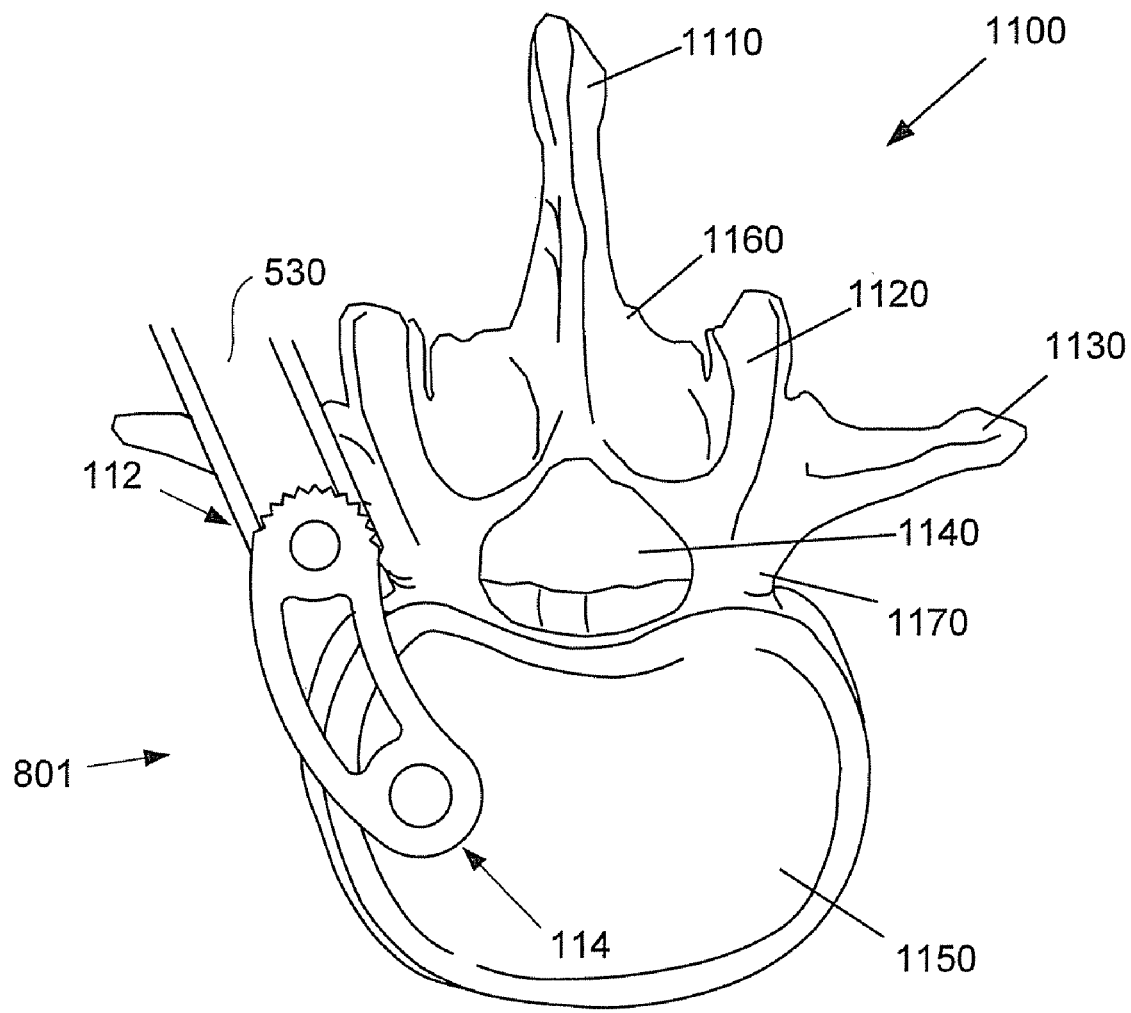
FIG. 11 is a side view of pivotably inserting an interbody spacer using the method of FIG. 10, according to various exemplary embodiments.

An exemplary method of inserting an interbody spacer using an insertion tool is described in FIG. 10 with reference to interaction between the interbody spacer as described in FIGS. 8A through 9B and the surgical process described in FIGS. 11 through 14. As illustrated in FIG. 10, the present exemplary method begins by the insertion instrument engaging the interbody spacer. As illustrated above, any number of rotatably coupling devices or configurations may be used to couple the interbody spacer. Consequently, depending on which insertion instrument is being used there are three initial steps to choose from (Step 10, 20, or 30). Specifically, a threaded male tip formed on the inserter may be threaded into a rotatable cylinder formed in the interbody spacer (step 10); an expandable tip may be placed into an access gap of an implant (step 20); or a threaded male tip coupled to an adapter may be threaded into a stationary threaded portion of a traditional implant (step 30). To initially engage the interbody spacer, the lever (520, FIG. 8A) is moved to the first position as shown in FIG. 8A. This allows the interbody spacer (801, FIG. 8A) to be attached to the insertion tool (802, FIG. 8B), while still allowing the interbody spacer (801, FIG. 8A) to be rotated. In other words, the interbody spacer is rotatably connected or coupled.

The spacer is then locked at the desired angle (Step 40). Once the insertion instrument (802, FIG. 8A) is engaged with the interbody spacer (801, FIG. 8A) in the desired orientation, the lever (520, FIG. 8A) is moved to the second position as shown in FIGS. 9A-9B. This pulls the rod (540, FIG. 5B, 740

FIG. 7B) up into the shaft (530, FIGS. 9A and 9B), which pulls the spacer teeth (120, FIG. 9B) into contact with the shaft teeth (560, FIG. 9B), thereby restraining the interbody spacer (801) from pivoting with respect to the insertion instrument (802).

The insertion instrument with the attached interbody spacer (801) is then inserted into the surgical site (Step 50). Now referring to FIG. 11, which illustrates the insertion of the interbody spacer (801) into the intervertebral space. The vertebra (1100) comprises a vertebral body (1150); a transverse process (1130) connected to the vertebral body by a pedicle (1170); a superior articular facet (1120) connected to the spinous process (1110) by a lamina (1160). The spinal canal (1140) passes between the pedicles (1170) anterior to the lamina (1160) and spinous process (1110). A plurality of nerve foramen (not shown) provides space for nerves to exit the spinal column.

In one exemplary embodiment, the interbody spacer is placed in the anterior space between adjoining vertebral bodies by the TLIF process. However, the present system and method may be used for any number of implant applications. As mentioned above, the TLIF process uses a posterior and lateral approach to access the disc space. To gain posterior and lateral access to the disc space, typically a facet joint is removed. The facet joint consists of a superior articular facet (1120) and the inferior articular facet (not shown) of the adjoining vertebra. The required amount of bone removal is determined by the surgeon and varies from patient to patient. The removal of the facet joint allows access via the nerve foramen to the intervertebral space between the two vertebral bodies. After preparatory surgical procedures are performed, the interbody spacer (801) is inserted using the insertion instrument (802).

The spacer (801) enters the surgical site with the distal end (114) leading. As mentioned above, the distal end (114) has a double elliptical shape, which eases the insertion of the spacer into the surgical site.

Figure 12:
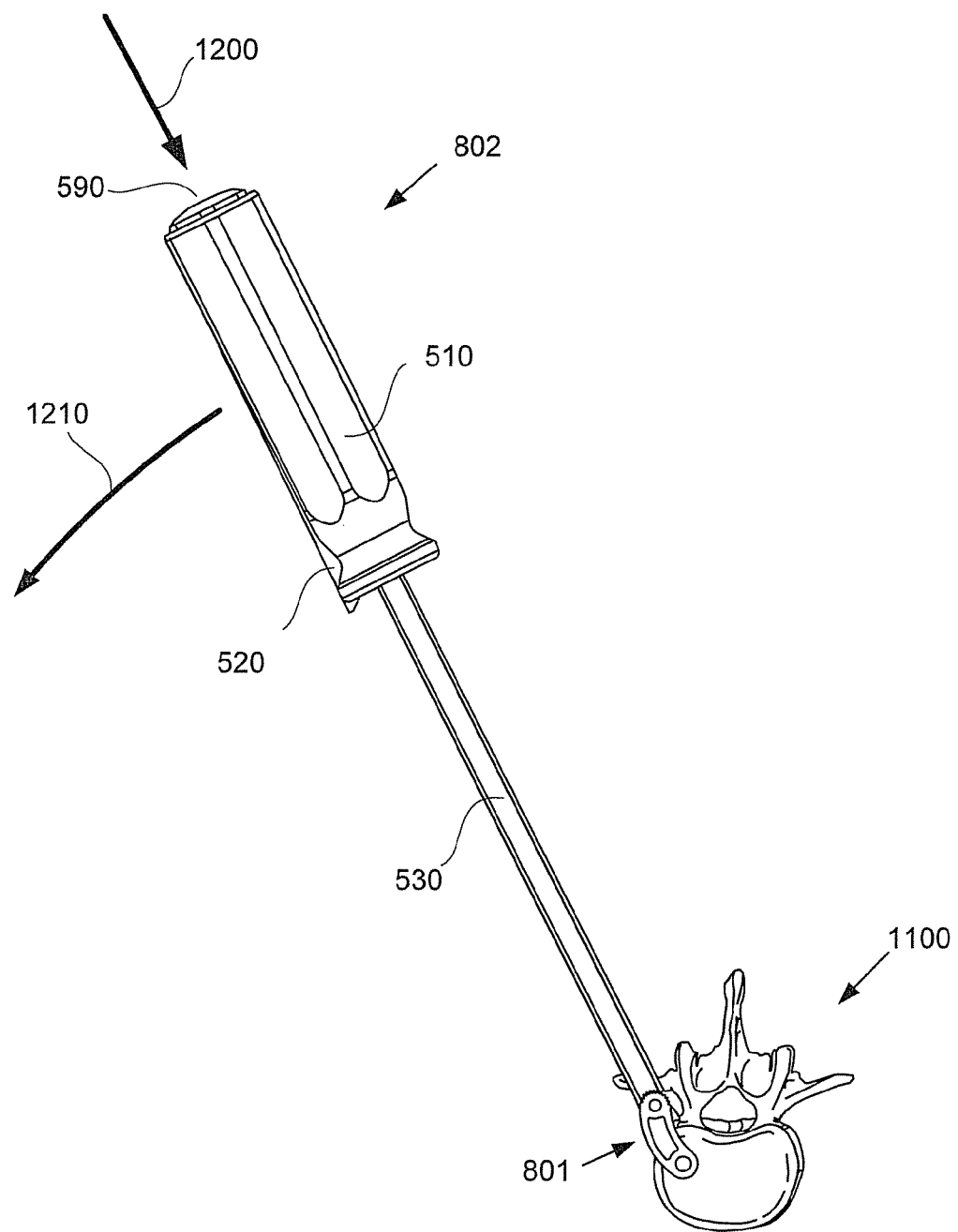
FIG. 12 is a side view of pivotably inserting an interbody spacer using the method of FIG. 10, according to various exemplary embodiments.

As shown in FIG. 12, the interbody spacer (801) may be inserted using a combination of impaction and rotation (Step 60, FIG. 10). Impaction typically involves striking the impaction cap (590) on the end of handle, either manually or with another instrument as indicated by the straight arrow (1200). The curved arrow (1210) shows a rigid body rotation of the insertion instrument (801) and the fixably attached interbody spacer (801).

Once the spacer (801) can no longer be inserted in its coupled state, the spacer (801) may be pivoted to allow for further insertion (Step 70, FIG. 10). To pivot the spacer about the end of the insertion instrument (802) the lever is moved to the first position, which disengages the matching teeth (120, 560, FIG. 8) as shown in FIG. 8.

Figures 13A, 13B:
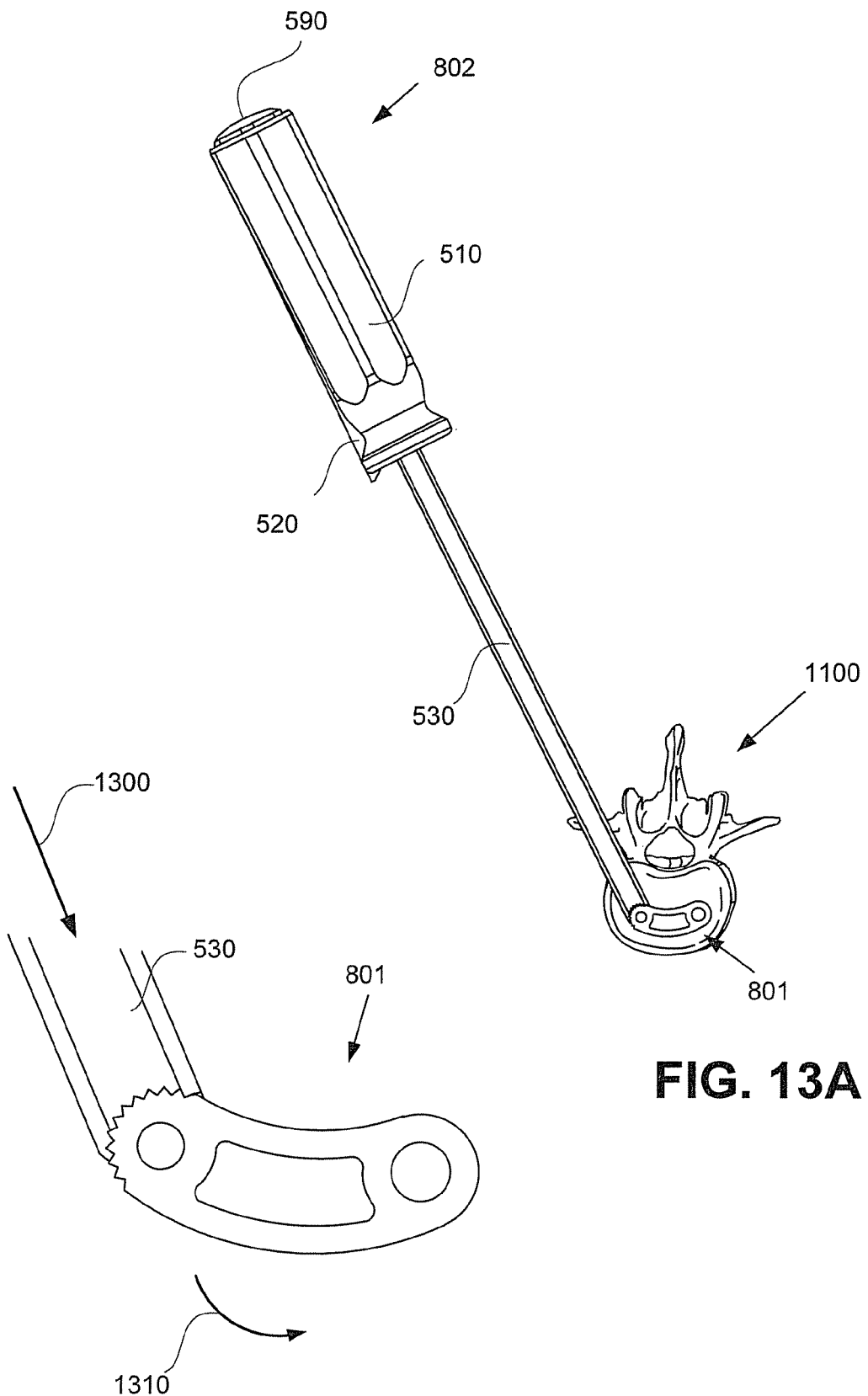
FIGS. 13A and 13B are side views of pivotable inserting an interbody spacer using the method of FIG. 10, according to various exemplary embodiments.

The insertion instrument can then be pivoted with respect to the partially inserted spacer (801) as shown in FIG. 13. The lever (520) is then returned to the second position. FIG. 13B shows the interbody spacer locked into a new angular position after the pivoting process. By pivoting the spacer (801), obstacles can be avoided and narrow or non-linear passageways can be followed without tamping the spacer into place. If required, the spacer can then be further inserted by impacting the insertion instrument as shown by the straight arrow (1300) and by further rotation as shown by the curved arrow (1310). The steps of pivoting and inserting the spacer are continued until the spacer is in its final position (Step 80, FIG. 10).

Figure 14:
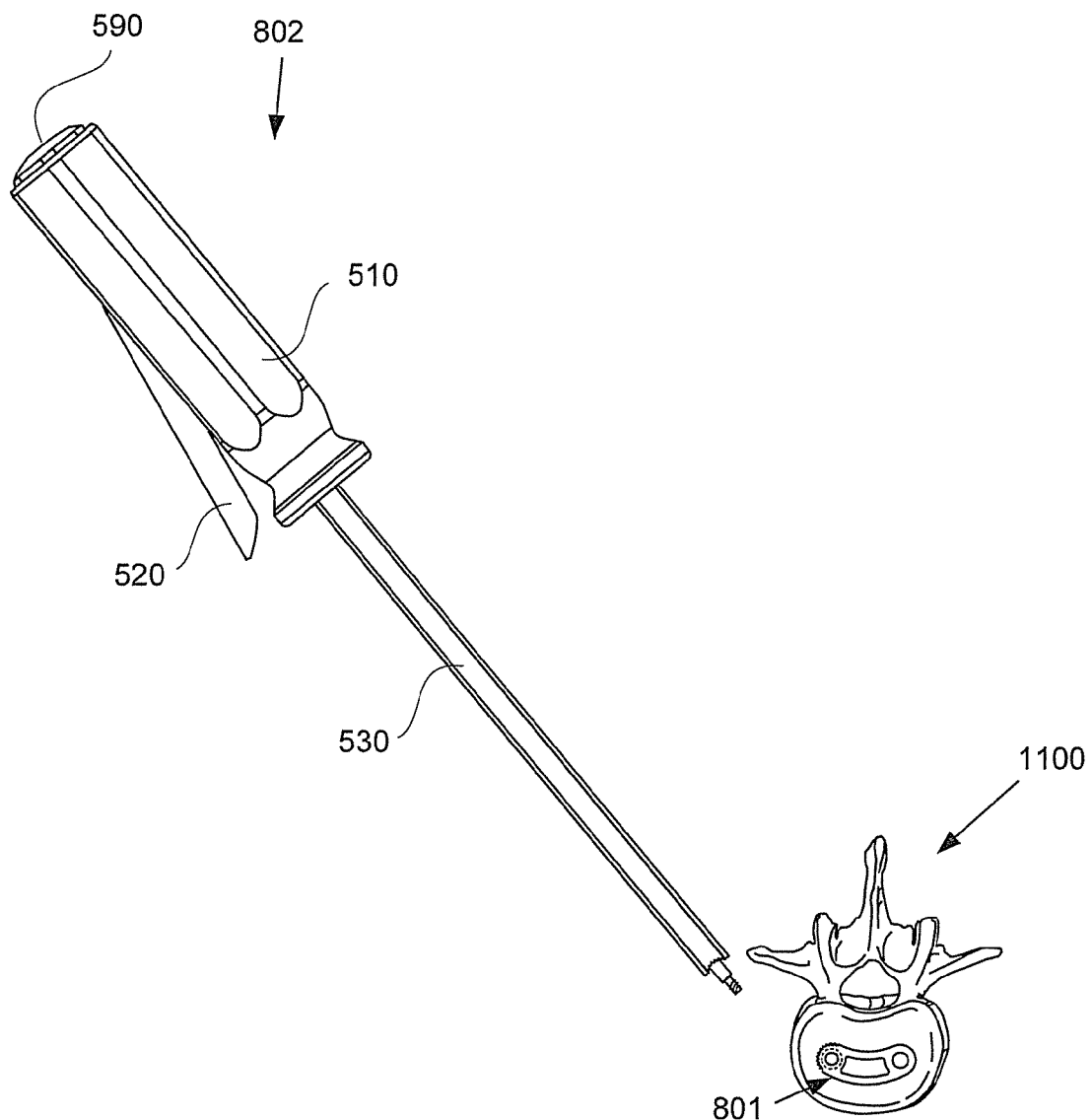
FIG. 14 is a side view of an interbody spacer in place and the insertion instrument being disengaged and withdrawn, according to one exemplary embodiment.

FIG. 14 illustrates the releasing of the spacer and the removal of the insertion instrument (step 9, 10, or 11, FIG. 10), accomplished by unthreading or contracting the expandable tip depending on which insertion tool is used. Once in a final position, the interbody spacer (801) is released from the insertion instrument (802). The insertion instrument (802) is removed from the patient, leaving the interbody spacer (801) correctly positioned within the surgical site.

In conclusion, the present exemplary systems and methods provide for a pivotable interbody spacer that provides a user with the ability to insert the spacer in a non-linear path. The insertion instrument can lock onto the interbody spacer at multiple angles to allow for the spacer to be pivoted in increments if the instrument rotation is restricted such that the instrument can only be rotated less that the total rotation implemented to position the spacer. This additional surgical flexibility can allow insertion of the interbody spacer with the removal of less tissue and bone which results in a less invasive surgery, fewer post operative complications, and quicker patient recovery time.

Additionally, the present exemplary interbody spacer (200, FIG. 2; 300, FIG. 3) employs geometry that provides for a small spacer with relatively large surface area and internal cavity. The spacer is hollowed out to increase cavity volume and surface area while minimizing overall size. Additionally the present exemplary systems and methods allow for rotation of the spacer for final positioning without having to release the spacer and tamp the spacer into place. Because the insertion instrument is not required to be disengaged from the spacer, quicker and simpler surgeries are possible.

By utilizing the insertion tool of FIG. 4, traditional interbody spacers may be coupled to the insertion instrument enabling them to be rotatably implanted. This allows for existing spacers to be used with the many of the benefits described above, such as a less invasive surgery.

The preceding description has been presented only to illustrate and describe the present methods and systems. It is not intended to be exhaustive or to limit the present system and method to any precise form disclosed. Many modifications and variations are possible in light of the above teaching.

The foregoing embodiments were chosen and described in order to illustrate principles of the system and method as well as some practical applications. The preceding description enables others skilled in the art to utilize the method and system in various embodiments and with various modifications as are suited to the particular use contemplated. It is intended that the scope of the present exemplary system and method be defined by the following claims.

What we claim is:

1. A spinal spacer system comprising:
    an interbody spacer, said interbody spacer includes a proximal end, a distal end, and a rotatably coupleable engagement member disposed on said proximal end of said spacer; and
    an insertion instrument, said insertion instrument including a handle member, an extension member including a first and a second end, wherein said first end of said extension member is coupled to said handle member, a coupling device configured to selectively couple said interbody spacer to said second end of said extension member, said coupling device comprises a single protruding member extending from said second end of said extension member, said protruding member comprises a threaded member,
    an actuator configured to selectively actuate said coupling device
    at least one joint in said threaded member; and
    an adaptor member including a proximal edge and a distal edge, said proximal edge including at least one frictionally engaging member and said distal edge including a concave spacer receiving surface;
wherein said threaded member passes through said adapter.

2. The spinal spacer system of claim 1 wherein said actuator is coupled to said protruding member;
wherein said actuator is configured to selectively retract said protruding member.

3. The spinal spacer system of claim 2, wherein said actuator is configured to be positioned in at least a first and a second actuation position;
wherein said first actuation position disposes said protruding member in an extended position; and
wherein said second actuation position disposes said protruding member in a retracted position.

4. The spinal spacer system of claim 3, including
at least one engagement member formed on said second end of said extension member; and
at least one frictional engagement member formed on said proximal end of said spacer;
wherein said at least one engagement member and said at least one frictional engagement member are configured to engage and frictionally secure said spacer relative to said handle member.

5. The spinal spacer system of claim 4, wherein:
said at least one engagement member comprises a first plurality of teeth; and
said at least one frictional engagement member comprises a second plurality of teeth.

6. The spinal spacer system of claim 1, wherein said rotatably coupeable engagement member comprises a cylinder;
said cylinder including a plurality of threads configured to engage with said protruding member.

7. The spinal spacer system of claim 6, wherein said interbody spacer includes frictional features disposed on said proximal end, said frictional features configured to selectively engage engagement features on said second end of said extension member to selectively fix an angular position of said interbody spacer relative to said handle member.

8. A method for inserting an interbody spacer into a surgical site with a selectively engageable insertion instrument, comprising:
creating a rotatably coupled connection between said interbody spacer and said selectively engageable insertion instrument by a single engagement protrusion from said selectively engageable insertion instrument;
said rotatably coupled connection includes a first threaded member disposed on said insertion instrument, said first threaded member being jointed, an adapter slidably coupled to said first threaded member; and a second threaded member disposed on said interbody spacer, wherein said second threaded member is configured to matingly receive said first threaded member;
fixing said interbody spacer in a first angular orientation with respect to said insertion instrument;
selectively engaging a first frictional feature on said interbody spacer with a portion of said insertion instrument;
selectively engaging said first frictional feature with a second frictional feature disposed on said insertion instrument by retracting said rotatably coupled connection toward said insertion instrument;
inserting said interbody spacer into said surgical site;
releasing said interbody spacer from said first angular position while maintaining said rotatably coupled connection;
pivoting said insertion instrument relative to said coupled connection such that said interbody spacer is in a second angular position with respect to said insertion instrument;
fixing said interbody spacer in said second angular position; and
further inserting said interbody spacer.

9. The method of claim 8, wherein said rotatably coupled connection comprises a first threaded member on said insertion instrument, said first threaded member matingly engaging a corresponding second threaded member disposed on said interbody spacer.

10. The method of claim 8, wherein said rotatably coupled connection comprises an expandable member disposed on an end of said insertion instrument, said expandable member coupling to a corresponding receiving orifice defined by said interbody spacer.

11. The method of claim 8, wherein said fixing said interbody spacer in a first angular orientation comprises selectively engaging a frictional feature on said adapter with a corresponding frictional feature disposed on said insertion instrument.

* * * * *